(12) United States Patent
Katayama et al.

(10) Patent No.: US 11,220,585 B2
(45) Date of Patent: Jan. 11, 2022

(54) HOLLOW PARTICLES AND USE OF SAME

(71) Applicant: SEKISUI PLASTICS CO., LTD., Osaka (JP)

(72) Inventors: Yugo Katayama, Nara (JP); Haruhiko Matsuura, Nara (JP)

(73) Assignee: SEKISUI PLASTICS CO., LTD., Osaka (JP)

(*) Notice: Subject to any disclaimer, the term of this patent is extended or adjusted under 35 U.S.C. 154(b) by 0 days.

(21) Appl. No.: 16/086,472

(22) PCT Filed: Jul. 7, 2016

(86) PCT No.: PCT/JP2016/070157
§ 371 (c)(1),
(2) Date: Sep. 19, 2018

(87) PCT Pub. No.: WO2017/163439
PCT Pub. Date: Sep. 28, 2017

(65) Prior Publication Data
US 2019/0100637 A1    Apr. 4, 2019

(30) Foreign Application Priority Data

Mar. 22, 2016    (JP) .............................. JP2016-057134

(51) Int. Cl.
*C08J 7/16*    (2006.01)
*C08J 7/14*    (2006.01)
(Continued)

(52) U.S. Cl.
CPC .................. *C08J 7/16* (2013.01); *C08F 2/28* (2013.01); *C08F 20/28* (2013.01); *C08F 20/32* (2013.01); *C08G 63/695* (2013.01); *C08G 73/02* (2013.01); *C08J 3/12* (2013.01); *C08J 7/14* (2013.01); *C08J 9/286* (2013.01); *C09D 7/65* (2018.01); *C09D 7/67* (2018.01); *C09D 7/68* (2018.01); *C09D 7/70* (2018.01); *B82Y 40/00* (2013.01); *C08J 2333/14* (2013.01); *C08J 2379/02* (2013.01); *C08K 5/17* (2013.01)

(58) Field of Classification Search
CPC .............................. B29C 64/10; A61K 8/0279
See application file for complete search history.

(56) References Cited

U.S. PATENT DOCUMENTS 4,548,196 A    10/1985  Torobin
2007/0251422 A1    11/2007  Maenaka et al.
(Continued)

FOREIGN PATENT DOCUMENTS

JP    61-187904    8/1986
JP    2002-80503    3/2002
(Continued)

OTHER PUBLICATIONS

Machine translation JP 2010-32719 (Year: 2010).*
(Continued)

*Primary Examiner* — Alexandre F Ferre
(74) *Attorney, Agent, or Firm* — Wenderoth, Lind & Ponack, L.L.P.

(57) ABSTRACT

Hollow particles each having a shell composed of at least one layer, wherein the at least one layer contains a nitrogen atom-containing resin having a refractive index of 1.57 or less.

19 Claims, 1 Drawing Sheet

(51) Int. Cl.
| | |
|---|---|
| *C08J 9/28* | (2006.01) |
| *C08F 20/32* | (2006.01) |
| *C08F 20/28* | (2006.01) |
| *C08F 2/28* | (2006.01) |
| *C08G 63/695* | (2006.01) |
| *C08G 73/02* | (2006.01) |
| *C09D 7/40* | (2018.01) |
| *C09D 7/65* | (2018.01) |
| *C08J 3/12* | (2006.01) |
| *B82Y 40/00* | (2011.01) |
| *C08K 5/17* | (2006.01) |

(56) References Cited

U.S. PATENT DOCUMENTS

| | | | |
|---|---|---|---|
| 2008/0057227 A1* | 3/2008 | Suzuki | C08B 3/06 428/1.1 |
| 2011/0020648 A1 | 1/2011 | Fukazawa et al. | |
| 2017/0114243 A1 | 4/2017 | Katayama et al. | |

FOREIGN PATENT DOCUMENTS

| | | |
|---|---|---|
| JP | 2005-215315 | 8/2005 |
| JP | 2006-089648 | 4/2006 |
| JP | 2007-75698 | 3/2007 |
| JP | 2007-291359 | 11/2007 |
| JP | 2009-80196 | 4/2009 |
| JP | 2010-32719 | 2/2010 |
| JP | 2014-198845 | 10/2014 |
| WO | WO2005/097870 | 10/2005 |
| WO | WO2016/111314 | 7/2016 |

OTHER PUBLICATIONS

Japanese Office Action in counterpart Application No. 2018-506747, dated Sep. 10, 2019 (along with a machine English-language translation).

International Search Report in International Bureau of WIPO Patent Application No. PCT/JP2016/070157, dated Sep. 6, 2016, along with an English-language translation thereof.

* cited by examiner

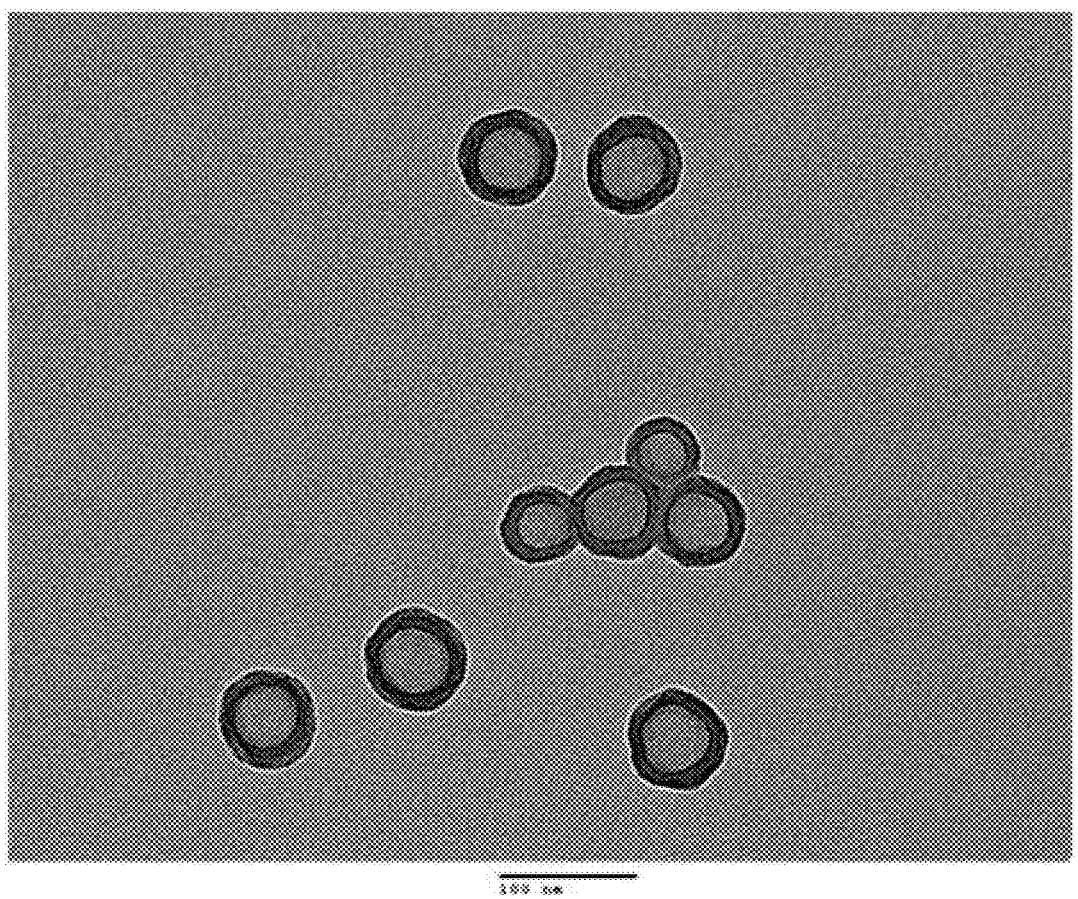

HOLLOW PARTICLES AND USE OF SAME

TECHNICAL FIELD

The present invention relates to hollow particles and use of same. More particularly, the present invention relates to hollow particles that have a small particle diameter, have high monodispersity, and generate a small number of pinholes in a shell, and use of same.

BACKGROUND TECHNOLOGY

Particles having pores in the interior thereof are used as microcapsule particles by incorporating various substances in the pores. Furthermore, particles (having hollows surrounded by shells) in which the pores are hollow, are named hollow particles, and the hollow particles are used as optical scattering materials, low reflection materials, heat-insulating materials or the like.

As a method for producing the hollow particles, for example, Japanese Unexamined Patent Application, First Publication No. 2002-80503 (Patent Document 1) and Japanese Unexamined Patent Application, First Publication No. 2005-215315 (Patent Document 2) describe a method for producing hollow particles by preparing oil droplets containing a poorly water-soluble organic solvent having low compatibility with a radical reactive monomer and a polymer of a radical reactive monomer in a water solvent, and after that, polymerizing the monomer.

Furthermore, International Publication No. WO2005/097870 (Patent Document 3) describes organic-inorganic hybrid hollow particles obtained by emulsifying a reaction solution containing a monomer, a reactive silane coupling agent, a non-reactive solvent, and a polymerization initiator in a polar solvent, and polymerizing the monomer, and organic-inorganic hybrid hollow particles obtained by emulsifying a mixed solution composed of an epoxy prepolymer and a non-reactive solvent in a polar solvent, adding polyamine, after that, polymerizing the monomer, and inorganically crosslinking the resulting hollow particles with a silane coupling agent having an amine group. In addition, "organic-inorganic" herein means that silicon is used as an inorganic component, and a resin other than silicon is used as an organic component.

PRIOR ART DOCUMENTS

Patent Documents

Patent Document 1: Japanese Unexamined Patent Application. First Publication No. 2002-80503
Patent Document 2: Japanese Unexamined Patent Application, First Publication No. 2005-215315
Patent Document 3: International Publication No. WO02005/097870

SUMMARY OF THE INVENTION

Problem to be Solved by the Invention

The hollow particles are used with a low-molecular binder component, in intended use such as optical scattering materials, low reflection materials, and heat-insulating materials. In the hollow particles described in the above-mentioned three Patent Documents, many pinholes are generated in shells. For that reason, when these hollow particles are used in the above-mentioned intended use, the binder component easily enters inside the hollows. As a result, a problem is that, the hollow particles cannot exert desired properties (light scattering property, heat insulating property, light reflectivity, and the like).

Means for Solving the Problem

Thus, according to the present invention, there is provided hollow particles each having a shell composed of at least one layer, wherein the at least one layer contains a nitrogen atom-containing resin having a refractive index of 1.57 or less.

Also, according to the present invention, there is provided a dispersion comprising the hollow particles.

Furthermore, according to the present invention, there is provided a coating agent comprising the hollow particles.

Additionally, according to the present invention, there is provided a heat-insulating film comprising the hollow particles.

Effects of Invention

According to the present invention, there can be provided hollow particles which have a small particle diameter, have high monodispersity, and are suitable for preparing a film having the low reflectance.

According to the present invention, when the hollow particles have any of the following aspects, there can be provided hollow particles which are more suitable for preparing a film having the lower reflectance, and have high monodispersity.

(1) The nitrogen atom-containing resin has an abundance ratio N of a nitrogen atom and an abundance ratio C of a carbon atom satisfying a relationship of $0.03 \leq N/C \leq 0.2$ in measurement by XPS (X-ray photoelectron spectroscopic analytical method).

(2) The nitrogen atom-containing resin is an organic-inorganic hybrid resin also containing a silicon component.

(3) The hollow particles have an average particle diameter of 10 to 150 nm.

(4) The nitrogen atom-containing resin is a nitrogen atom-containing vinyl-based resin composed of a vinyl-based monomer.

(5) The hollow particles each have a surface treated with a compound having at least one anionic group.

(6) The compound having an anionic group is selected from hydrochloric acid, an oxo acid, and a derivative of these acids.

(7) The compound having an anionic group is selected from a carboxylic acid compound, a sulfonic acid compound, and a phosphoric acid ester compound.

BRIEF DESCRIPTION OF TIE DRAWINGS

FIG. 1 is a photograph of the hollow particles of Example 1.

BEST MODE FOR CARRYING OUT THE INVENTION

The hollow particles each have a shell composed of at least one layer. A layer constituting the shell may be composed of one layer, or may be composed of two or more plural layers (for example, two layers, three layers, four layers).

The at least one layer contains a nitrogen atom-containing resin (hereinafter, also referred to as N-containing resin)

having a refractive index of 1.57 or less. Since the hollow particles having a layer containing the N-containing resin having a refractive index of 1.57 or less hardly hinder the progress of light when used as low refractive index materials, the particles exhibit high transparency. The shell may be composed only of one layer containing the N-containing resin.

If a refractive index of the N-containing resin exceeds 1.57, since a refractive index of the resulting hollow particles becomes high, a refractive index may not be sufficiently reduced when the hollow particles are used in low refractive index materials. When the hollow particles are used in low refractive index materials, since a lower refractive index of the N-containing resin is more preferable, a lower limit does not exist. A refractive index of the N-containing resin is more preferably 1.56 or less, and further preferably 1.55 or less.

It is preferable that the N-containing resin has an abundance ratio N of a nitrogen atom and an abundance ratio C of a carbon atom satisfying a relationship of $0.03 \leq N/C \leq 0.2$, in measurement by XPS (X-ray photoelectron spectroscopic analytical method). Here, "N/C" means the ratio of an "N" atom in a component derived from a monomer having an N-containing substituent such as an amino group, and a "C" atom constituting the N-containing resin. Additionally, the monomer having the N-containing substituent mainly derives from a crosslinking monomer, as described below. If N/C is less than 0.03, the crosslinking density becomes low, and a low-molecular binder component may become easy to enter inside hollows. If N/C exceeds 0.2, since the crosslinking density is too high, pinholes become easy to be generated, and a low-molecular binder component may become easy to enter inside hollows. N/C can take 0.03, 0.04, 0.05, 0.06, 0.07, 0.08, 0.09, 0.1, 0.13, 0.15, 0.18, and 0.2. N/C is more preferably 0.03 to 0.15, and further preferably 0.03 to 0.1.

Furthermore, it is preferable that the hollow particles have an average particle diameter of 10 to 150 nm. In the hollow particles having an average particle diameter of less than 10 nm, aggregation between the hollow particles is generated, and handleability may be inferior. In the hollow particles having an average particle diameter more than 150 nm, when kneaded with a coating agent or a resin, scattering at irregularities of the surface or a particle interface becomes great, and the particles may be whitened. An average particle diameter can take 10 nm, 20 nm, 30 nm, 50 nm, 80 nm, 100 nm, 120 nm, and 150 nm. An average particle diameter is more preferably 30 to 100 nm, and an average particle diameter is further preferably 30 to 80 nm.

It is preferable that the N-containing resin is a nitrogen atom-containing vinyl-based resin composed of a vinyl-based monomer. In particular, since the nitrogen atom-containing vinyl-based resin composed of a vinyl-based monomer having no aromatic ring has high weather resistance, and can suppress yellowing and the like with time, it is preferable.

In the hollow particles, a CV value that is an index of assessment of monodispersity is preferably 30% or less, more preferably 25% or less, and further preferably 20% or less.

It is preferable that the hollow particles have a hollow ratio of 10 to 90%. If a hollow ratio is less than 10%, a hollow part is small, and desired properties may not be obtained. If a hollow ratio is greater than 90%, a hollow part becomes too great, and the strength of the hollow particles may be reduced. A hollow ratio can take 10%, 20%, 30%, 40%, 50%, 60%, 70%, 80%, and 90%. A more preferable hollow ratio is 10 to 80%, and a further preferable hollow ratio is 10 to 70%.

It is preferable that the number of pinholes in the shell of the hollow particles is small. If the number of pinholes in the shell is large, a low-molecular binder component easily enters inside hollows, when these particles are used in members for which heat conductivity is desired to be adjusted. For that reason, when the hollow particles are used in low refractive index materials, a refractive index may not be sufficiently reduced, and when used as heat conductivity adjusting agents, heat conductivity may not be adjusted.

The N-containing resin is preferably a polymer that a polymer of a radical reactive monomer having at least one epoxy group or oxetane group is crosslinked with a nitrogen atom-containing crosslinking monomer such as a polyamine-based compound.

The N-containing resin is preferably an N-containing vinyl-based resin that a polymer obtained by polymerizing at least one monomer having a radical reactive functional group such as a vinyl group, a (meth)acryloyl group, an allyl group, a maleoyl group, a fumaroyl group, a styryl group, and a cinnamoyl group, or a copolymer obtained by copolymerizing the at least one monomer, is crosslinked with a nitrogen atom-containing crosslinking monomer, such as a polyamine-based compound.

The content of the N-containing resin in the hollow particles is preferably 5 to 100 parts by mass, based on 100 parts by mass of the hollow particles. If the content is less than 5 parts by mass, dispersibility into an organic binder that is used for preparing heat-insulating paints is deteriorated, and a coated film may be easily whitened. The content of the N-containing resin can take 5 parts by mass, 10 parts by mass, 30 parts by mass, 50 parts by mass, 70 parts by mass, 90 parts by mass, and 100 parts by mass. The content of the N-containing resin is more preferably 10 to 100 parts by mass, and further preferably 50 to 100 parts by mass, based on 100 parts by mass of the hollow particles.

As the N-containing resin, various resins can be used, and among them, an organic-inorganic hybrid resin containing a silicon component (hereinafter, referred to as Si & N-containing resin) is preferable.

The Si & N-containing resin is preferably a Si & N-containing vinyl-based resin that a polymer obtained by polymerizing at least one monomer having a radical reactive functional group such as a vinyl group, a (meth)acryloyl group, an allyl group, a maleoyl group, a fumaroyl group, a styryl group, and a cinnamoyl group, or a copolymer obtained by copolymerizing the at least one monomer, is crosslinked with a nitrogen atom-containing crosslinking monomer, such as a polyamine-based compound.

The Si & N-containing resin is preferably a copolymer that a copolymer derived from a radical reactive monomer having at least one epoxy group or oxetane group, and a radical reactive monomer having at least one silyl group is crosslinked with a nitrogen atom-containing crosslinking monomer, such as a polyamine-based compound. In addition, an epoxy group, an oxetane group, and a silyl group are collectively also referred to as a non-radical reactive functional group.

Furthermore, a refractive index of the Si & N-containing resin is preferably 1.57 or less. If a refractive index of the Si & N-containing resin exceeds 1.57, since a refractive index of the resulting hollow particles becomes high, a refractive index may not be sufficiently reduced when the hollow particles are used in low refractive index materials. When the hollow particles are used in low refractive index materials, since a lower refractive index of the Si & N-containing resin is more preferable, a lower limit does not exist. A refractive index of the Si & N-containing resin is more preferably 1.56 or less, and further preferably 1.55 or less.

Furthermore, it is preferable that the Si & N-containing resin has the abundance ratio of a silicon atom, Si, and the abundance ratio of a carbon atom, C, satisfying a relationship of $0.001 \leq Si/C \leq 0.1$, in measurement by XPS. If Si/C is less than 0.001, the crosslinking density becomes low, and a low-molecular binder component may become easy to enter inside hollows. If Si/C exceeds 0.1, since the crosslinking density is too high, pinholes become easy to be generated, and a low-molecular binder component may become easy to enter inside hollows. Si/C can take 0.001, 0.002, 0.005, 0.01, 0.02, 0.03, 0.05, 0.06, 0.07, 0.08, 0.09, and 0.1. Si/C is more preferably 0.002 to 0.05, and further preferably 0.002 to 0.02.

(1) Radical Reactive Monomer Having Epoxy Group or Oxetane Group

A radical reactive monomer having at least one epoxy group or oxetane group has an epoxy group or an oxetane group, and a radical reactive functional group.

The radical reactive functional group is not particularly limited, as long as it is an ethylenic unsaturated group that is reacted in radical polymerization. Examples thereof include a vinyl group, a (meth)acryloyl group, an allyl group, a maleoyl group, a fumaroyl group, a styryl group, a cinnamoyl group, and the like. Inter ala, a vinyl group, a (meth)acryloyl group, and an allyl group, of which control of reactivity is easy, are preferable.

An epoxy group or an oxetane group is a functional group that is reacted with a compound having an amino group, a carboxy group, a chlorosulfone group, a mercapto group, a hydroxy group, an isocyanate group or the like, to generate a polymer.

The reactive monomer having a radical reactive functional group, and an epoxy group or oxetane group is not particularly limited. Examples thereof include p-glycidyl-styrene, glycidyl (meth)acrylate, 4-hydroxybutyl (meth) acrylate glycidyl ether, (3-ethyloxetan-3-yl)methyl (meth) acrylate, 3,4-epoxycyclohexylmethyl (meth)acrylate, and the like. Only one of these monomers may be used, or two or more of them may be used concurrently.

(2) Radical Reactive Monomer Having Silyl Group

A radical reactive monomer having at least one silyl group has a silyl group and a radical reactive functional group.

The radical reactive functional group is not particularly limited, as long as it is an ethylenic unsaturated group that is reacted in radical polymerization Examples thereof include a vinyl group, a (meth)acryloyl group, an allyl group, a maleoyl group, a fumaroyl group, a styryl group, a cinnamoyl group, and the like. Inter alia, a vinyl group, a (meth)acryloyl group, and an allyl group, of which control of reactivity is easy, are preferable.

The reactive monomer having a silyl group and a radical reactive functional group is not particularly limited. Examples thereof include vinyltrichlorosilane, vinyltrimethoxysilane, vinyltriethoxysilane, p-styrylmethoxysilane, 3-methacryloxypropyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, and the like. Only one of these monomers may be used, or two or more of them may be used concurrently.

(3) Copolymer Composed of Radical Reactive Monomer Having Epoxy Group or Oxetane Group, and Radical Reactive Monomer Having Silyl Group In the above-mentioned copolymer, the ratio (ratio by mass) of a component derived from a radical reactive monomer having an epoxy group or oxetane group and that derived from a radical reactive monomer having a silyl group is preferably 1:100 to 0.001. If the ratio of the component derived from a radical reactive monomer having a silyl group is less than 0.001, the strength of the shell reduces, and the hollow particles may collapse, or the hollow particles may not be obtained. If the ratio is greater than 100, the shell becomes too brittle, and it may become difficult to enhance heat insulating property of a film due to easy generation of pinholes. The ratio can take 1:100, 80, 50, 30, 10, 5, 1, 0.1, 0.05, 0.01, 0.005, and 0.001. The more preferable ratio is 1:10 to 0.001, and the further preferable ratio is 1:1 to 0.01.

(4) Monofunctional Monomer

A polymer composed of the radical reactive monomer having an epoxy group or oxetane group may contain a component derived from a monofunctional monomer having only one reactive functional group. Examples of the monofunctional monomer include styrene, esters of (meth)acrylic acid and alcohols having 1 to 25 carbon atoms, and the like.

Examples of the ester of (meth)acrylic acid and alcohols having 1 to 25 carbon atoms include methyl (meth)acrylate, ethyl (meth)acrylate, propyl (meth)acrylate, n-butyl (meth) acrylate, isobutyl (meth)acrylate, tertiary butyl (meth)acrylate, pentyl (meth)acrylate, (cyclo)hexyl (meth)acrylate, heptyl (meth)acrylate, (iso)octyl (meth)acrylate, nonyl (meth)acrylate, (iso)decyl (meth)acrylate, norbornyl (meth) acrylate, isobornyl (meth)acrylate, adamantyl (meth)acrylate, lauryl (meth)acrylate, tetradecyl (meth)acrylate, (iso) stearyl (meth)acrylate, phenoxyethylene glycol (meth) acrylate, phenoxydiethylene glycol (meth)acrylate, 2-ethylhexyl (meth)acrylate, and the like.

Only one of the monofunctional monomers may be used, or two or more of them may be used concurrently.

The content of a component derived from the radical reactive monomer having an epoxy group or oxetane group and that derived from the radical reactive monomer having a silyl group is preferably 10% by mass or more, based on a total of components derived from the reactive monomers. If the content is less than 10% by mass, the hollow particles may not be obtained. This content can take 10% by mass, 30% by mass, 50% by mass, 60% by mass, 80% by mass, and 100% by mass. This content is more preferably 30% by mass or more, and further preferably 50% by mass or more.

(5) Crosslinking Monomer

The N-containing resin contains a component derived from a nitrogen atom-containing crosslinking monomer such as a polyamine-based compound.

Examples of the polyamine-based compound include aliphatic amines such as ethylene diamine and adducts thereof, diethylenetriamine, dipropylenetriamine, triethylenetetramine, tetraethylenepentamine, dimethylaminopropylamine, diethylaminopropylamine, dibutylammopropylamine, hexamethylenediamine and modified products thereof. N-aminoethylpiperazine, bis-aminopropylpiperazine, trimethylhexamethylenediamine, bis-hexamethylenetriamine, dicyandiamide, diacetoacrylamide, various modified aliphatic polyamines, and polyoxypropylenediamine; alicyclic amines such as 3,3'-dimethyl-4,4'-diaminodicyclohexylmethane, 3-amino-1-cyclohexylaminopropane, 4,4'-diaminodicyclohexylmethane, isophoronediamine, 1,3-bis (aminomethyl)cyclohexane. N-dimethylcyclohexylamine, and bis(aminomethyl)norbornane, and modified products thereof;

aromatic amines such as 4,4'-diaminodiphenylmethane (methylenedianiline), 4,4'-diaminodiphenyl ether, diaminodiphenyl sulfone, m-phenylenediamine, 2,4'-toluylenediamine, m-toluylenediamine, o-toluylenediamine, meta-xylylenediamine, and xylylenediamine, and modified products thereof, and other special amine modified products; tertiary amines such as amido amine, poly(amido amine) such as aminopolyamide resins, dimethylaminomethylphenol, 2,4,6-tri(dimethylaminomethyl)phenol, and a tri-2-ethylhexane salt of tri(dimethylaminomethyl)phenol, and the like.

Only one of the above-mentioned crosslinking monomers may be used, or two or more of them may be used concurrently.

(6) Surface Treating Agent

The hollow particles each may have a surface treated with a compound having at least one anionic group. The surface treated with this compound imparts to the hollow particles heat resistance, dispersibility in an organic solvent, and a nature that a low-molecular binder component becomes difficult to enter inside hollows.

The compound having an anionic group is selected from hydrochloric acid, acid anhydride, and oxo acid (for example, inorganic acids such as nitric acid, phosphoric acid, sulfuric acid, and carbonic acid; and organic acids such as a carboxylic acid compound, an alkyl ester compound of sulfuric acid, a sulfonic acid compound, a phosphoric acid ester compound, a phosphonic acid compound, and a phosphinic acid compound).

The carboxylic acid compound is not particularly limited, as long as it is a compound containing a carboxyl group. Examples thereof include linear carboxylic acids such as formic acid, acetic acid, propionic acid, butyric acid, valeric acid, hexanoic acid, heptanoic acid, octanoic acid, nonanoic acid, decanoic acid, dodecanoic acid, tetradecanoic acid, and stearic acid; branched carboxylic acids such as pivalic acid, 2,2-dimethylbutyric acid, 3,3-dimethylbutyric acid, 2,2-dimethylvaleric acid, 2,2-diethylbutyric acid, 3,3-diethylbutyric acid, 2-ethylhexanoic acid, 2-methylheptanoic acid, 4-methyloctanoic acid, and neodecanoic acid; cyclic carboxylic acids such as naphthenic acid and cyclohexanedicarboxylic acid; and the like. In order to effectively enhance dispersibility in an organic solvent, among these, linear carboxylic acid, branched carboxylic acid and the like, having 4 to 20 carbon atoms, are preferable.

Furthermore, as the carboxylic acid compound, carboxylic acids having a radical reactive functional group such as a vinyl group, a (meth)acryloyl group, an allyl group, a maleoyl group, a fumaroyl group, a styryl group, and a cinnamoyl group can also be used. Examples thereof include acrylic acid, methacrylic acid, 2-acryloyloxyethylsuccinic acid, 2-methacryloyloxyethylsuccinic acid, 2-acryloyloxyethylhexahydrophthalic acid, 2-methacryloyloxyethyoxyethylhexahydrophthalic acid, 2-acryloyloxyethylphthalic acid, 2-methacryloyloxyethylphthalic acid, vinylbenzoic acid, and the like.

Examples of the alkyl ester compound of sulfuric acid include dodecylsulfuric acid and the like.

The sulfonic acid compound is not particularly limited, as long as it is a compound containing a sulfo group. Examples thereof include p-toluenesulfonic acid, benzenesulfonic acid, dodecylbenzenesulfonic acid, methylsulfonic acid, ethylsulfonic acid, vinylsulfonic acid, allylsulfonic acid, methallylsulfonic acid, 2-acrylamido-2-methylpropanesulfonic acid, and the like.

The phosphoric acid ester compound is not particularly limited, as long as it is an ester compound of phosphoric acid. For example, it is represented by the following general formula (I).

[Chemical formula 1]

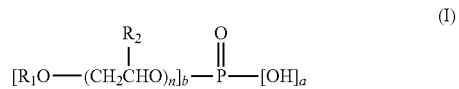

In the above-mentioned formula, $R_1$ is an alkyl group having 4 to 19 carbon atoms, an allyl group ($CH_2$=$CHCH_2$—), a (meth)acrylic group or a styryl group. Examples of the alkyl group having 4 to 19 carbon atoms include a butyl group, a pentyl group, an octyl group, a nonyl group, a decyl group, an undecyl group, a dodecyl group, a tridecyl group, and a stearyl group. These groups may be linear or branched. Additionally, only one of them may be used, or more than one of them may be used concurrently.

$R_2$ is H or $CH_3$.

n is the addition mole number of alkylene oxide, and is a numerical value in the necessary range for giving the addition mole number of 0 to 30, when the whole is set to be 1 mole. The addition mole number can take 0, 1, 5, 10, 15, 20, 25, and 30.

A combination of a and b is a combination of 1 and 2, or 2 and 1.

Alternatively, KAYAMER PM-21 of Nippon Kayaku Co., Ltd, and the like can also be used.

Furthermore, as the oxo acid, a polymer having an acid group can also be used. Examples thereof are not limited to, but include DISPERBYK 103, DISPERBYK 110, DISPERBYK 118, DISPERBYK 111, DISPERBYK 190, DISPERBYK 194N, DISPERBYK 2015 (all of the above manufactured by BYK Company); Solsperse 3000, Solsperse 21000, Solsperse 26000, Solsperse 36000, Solsperse 36600, Solsperse 41000, Solsperse 41090, Solsperse 43000, Solsperse 44000, Solsperse 46000, Solsperse 47000, Solsperse 53095, Solsperse 55000 (all of the above manufactured by Lubrizol Company); EFKA4401. EFKA4550 (manufactured by EFKA ADDITIVES Company); Floren G-600, Floren G-700, Floren G-900, Floren GW-1500, Floren GW-1640 (all of the above manufactured by KYOEISHA CHEMICAL Co., LTD.); DISPARLON 1210, DISPARLON 1220, DISPARLON 2100, DISPARLON 2150, DISPARLON 2200, DISPARLON DA-325, DISPARLON DA-375 (manufactured by Kusumoto Chemicals, Ltd.); AJISPER PB821, AJISPER PB822, AJISPER PB824, AJISPER PB881, AJISPER PN411 (manufactured by Ajinomoto Fine-Techno Co., Inc.); and the like.

Furthermore, surface treatment may be performed with a silicon-based compound, a titanate-based coupling agent, an aluminate-based coupling agent, a zirconate-based coupling agent, an isocyanate-based compound or the like, as necessary.

Examples of the above-mentioned silicon-based compound include alkoxysilanes such as methyltrimethoxysilane, dimethyldimethoxysilane, phenyltrimethoxysilane, methyltriethoxysilane, dimethyldiethoxysilane, phenyltriethoxysilane, n-propyl trimethoxysilane, n-propyltriethoxysilane, hexyltrimethoxysilane, hexyltriethoxysilane, octyltriethoxysilane, decyltrimethoxysilane, 1,6-bis(trimethoxysilyl)hexane, and trifluoropropyltrimethoxysilane; silazanes such as hexamethyldisilazane; chlorosilanes such as trimethylsilyl chloride; and silane coupling agents such as vinyltrimethoxysilane, vinyltriethoxysilane, 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxyprompyltrimethoxysilane, 3-methacryloxypropylmethyldiethoxysilane, 3-methacryloxypropyltriethoxysilane, 3-acryloxypropyltrimethoxysilane, N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane, tris-(trimethoxysilylpropyl)isocyanurate, 3-ureidopropyltrialkoxysilane, 3-mercaptopropylmethyldimethoxysilane, 3-mercaptopropyltrimethoxysilane, bis(triethoxysilylpropyl) tetrasulfide, and 3-isocyanatopropyltriethoxysilane, but the silicon-based compound used in the present invention is not limited to these.

Examples of the above-mentioned titanate-based coupling agent include PLENACT TTS, PLENACT 46B, PLENACT 55, PLENACT 41B, PLENACT 38S, PLENACT 138S, PLENACT 238S, PLENACT 338X, PLENACT 44, PLENACT 9SA, and PLENACT ET manufactured by Ajinomoto Fine-Techno Co., Inc., but the titanate-based coupling agent used in the present invention is not limited to these.

Examples of the above-mentioned aluminate-based coupling agent include PLENACT AL-M manufactured by Ajinomoto Fine-Techno Co., Inc., but the aluminate-based coupling agent used in the present invention is not limited to these.

Examples of the above-mentioned zirconate-based coupling agent include ORGATIX ZA-45, ORGATIX ZA-65, ORGATIX ZC-150, ORGATIX ZC-540, ORGATIX ZC-700, ORGATIX ZC-580, ORGATIX ZC-200, ORGATIX ZC-320, ORGATIX ZC-126, and ORGATIX ZC-300 manufactured by Matsumoto Fine Chemical Co., Ltd., but the zirconate-based coupling agent used in the present invention is not limited to these.

Examples of the above-mentioned isocyanate-based compound include ethyl isocyanate, propyl isocyanate, isopropyl isocyanate, butyl isocyanate, tert-butyl isocyanate, hexyl isocyanate, dodecyl isocyanate, octadecyl isocyanate, cyclohexyl isocyanate, benzyl isocyanate, phenyl isocyanate, 4-butylphenyl isocyanate, 2-isocyanatoethyl methacrylate, 2-isocyanatoethyl acrylate, and 1,1-(bisacryloyloxymethyl)ethyl isocyanate, but the isocyanate-based compound used in the present invention is not limited to these.

Only one of the above-mentioned surface treating agents may be used, or two or more of them may be used concurrently.

(7) Other Additives

The hollow particles may contain other additives such as pigment particles (pigments), dyes, stabilizers, ultraviolet absorbing agents, anti-foaming agents, thickeners, heat stabilizers, leveling agents, lubricants, and antistatic agents, as necessary, in the range that the effect of the present invention is not inhibited.

The pigment particles are not particularly limited, as long as they are pigment particles used in the art. Examples thereof include particles of iron oxide-based pigments such as micaceous iron oxide and iron black; lead oxide-based pigments such as red lead and chrome yellow; titanium oxide-based pigments such as titanium white (rutile-type titanium dioxide), titanium yellow, and titanium black; cobalt oxide; zinc oxide-based pigments such as zinc yellow; molybdenum oxide-based pigments such as molybdenum red and molybdenum white; and the like. Only one of the pigment particles may be used, or two or more of them may be used concurrently.

(8) Intended Use of Hollow Particles

The hollow particles are useful as additives of paints, papers, information recording papers, heat-insulating films, and thermoelectric conversion materials, which are such intended use that adjustment of the reflectance is desired. Furthermore, the hollow particles are also useful as additives for coating agents (compositions for coating) used in light diffusion films (optical sheets), light-guiding plate inks, antireflection films, light extraction films, and the like; additives of master pellets for forming molded articles such as light diffusion plates and light-guiding plates; and additives for cosmetics.

(a) Coating Agent

A coating agent contains at least the above-mentioned hollow particles. The coating agent may contain arbitrary binder.

The binder is not particularly limited, but the known binder resin can be used. Examples of the binder resin include thermosetting resins, thermoplastic resins, and the like, more specifically, fluorine-based resins, polyamide resins, acrylic resins, polyurethane resins, acrylic urethane resins, butyral resins, and the like. These binder resins may be used alone, or two or more of them may be used by mixing them. Furthermore, the binder resin may be a homopolymer of one reactive monomer, or may be a copolymer of a plurality of monomers. Furthermore, as the binder, a reactive monomer may be used.

Examples of the reactive monomer include monofunctional reactive monomers such as esters of (meth)acrylic acid and alcohols having 1 to 25 carbon atoms, such as methyl (meth)acrylate, ethyl (meth)acrylate, propyl (meth)acrylate, n-butyl (meth)acrylate, isobutyl (meth)acrylate, tertiary butyl (meth)acrylate, pentyl (meth)acrylate, (cyclo)hexyl (meth)acrylate, heptyl (meth)acrylate, (iso)octyl (meth)acrylate, nonyl (meth)acrylate, (iso)decyl (meth)acrylate, norbornyl (meth)acrylate, isobornyl (meth)acrylate, adamantyl (meth)acrylate, lauryl (meth)acrylate, tetradecyl (meth)acrylate. (iso)stearyl (meth)acrylate, phenoxyethylene glycol (meth)acrylate, phenoxydiethylene glycol (meth)acrylate, and 2-ethylhexyl (meth)acrylate; and polyfunctional reactive monomers such as trimethylolpropane tri(meth)acrylate, tripropylene glycol di(meth)acrylate, diethylene glycol di(meth)acrylate, dipropylene glycol di(meth)acrylate, pentaerythritol tri(meth)acrylate, pentaerythritol tetra(meth)acrylate, dipentaerythritol hexa(meth)acrylate, 1,6-hexanediol di(meth)acrylate, neopentyl glycol di(meth)acrylate, trimethylolpropane tri(meth)acrylate, ditrimethylolpropane tetra(meth)acrylate, dipentaerythritol penta(meth)acrylate, tripentaerythritol octa(meth)acrylate, tetrapentaerythritol deca(meth)acrylate, isocyanuric acid tri(meth)acrylate, isocyanuric acid di(meth)acrylate, polyester tri(meth)acrylate, polyester di(meth)acrylate, bisphenol di(meth)acrylate, diglycerin tetra(meth)acrylate, adamantyl di(meth)acrylate, isobornyl di(meth)acrylate, dicyclopentane di(meth)acrylate, tricyclodecane di(meth)acrylate, and ditrimethylolpropane tetra(meth)acrylate.

Furthermore, when these reactive monomers are used, a polymerization initiator that initiates a curing reaction by ionizing radiation may also be used. Examples thereof include imidazole derivatives, bisimidazole derivatives, N-arylglycine derivatives, organic azide compounds, titanocenes, aluminate complexes, organic peroxides, N-alkoxypyridinium salts, thioxanthone derivatives, and the like.

Furthermore, as the binder, for example, inorganic binders such as a hydrolysate of silicon alkoxide can also be used. Examples of the silicon alkoxide include tetramethoxysilane, tetraethoxysilane, methyltrimethoxysilane, methyltriethoxysilane, 3-aminopropyltrimethoxysilane, 3-aminopropyltriethoxysilane, 2-hydroxyethyltrimethoxysilane, 2-hydroxyethyltriethoxysilane, 2-hydroxypropyltrimethoxysilane, 2-hydroxypropyltriethoxysilane, 3-hydroxypropyltrimethoxysilane, 3-hydroxypropyltriethoxysilane, vinyltrimethoxysilane, vinyltriethoxysilane, vinyltriacetoxysilane, allyltrimethoxysilane, 3-acryloxypropyltrimethoxysilane, 3-methacryloxypropylmethyldimethoxysilane, 3-methacryloxytrimethoxysilane, 3-methacryloxypropylmethyldiethoxysilane, 3-methacryloxypropyltriethoxysilane, 3-mercaptopropyltrimethoxysilane, 3-mercaptopropylmethyldimethoxysilane, 3-mercaptopropyltriethoxysilane, 3-isocyanatopropyltrimethoxysilane, 3-isocyanatopropyltriethoxysilane, 3-glycidoxypropyltrimethoxysilane, 3-glycidoxypropyltriethoxysilane 2-(3,4-epoxycyclohexyl)ethyltrimethoxysilane, 2-(3,4-epoxycyclohexyl)ethyltriethoxysilane. 3-(meth) acryloxypropyltrimethoxysilane, 3-(meth)acryloxypropyltriethoxysilane, 3-ureidopropyltrimethoxysilane, 3-ureidopropyltriethoxysilane, dimethyldimethoxysilane, dimethyldiethoxysilane, diethyldimethoxysilane, and diethyldiethoxysilane.

Examples of the known binder product include DIANAL LR-102 and DIANAL BR-106 manufactured by MITSUBISHI RAYON CO., LTD., and the like.

The content of the hollow particles in the coating agent is appropriately adjusted depending on application thereof, and the hollow particles can be used in the range of 0.1 to 1,000 parts by mass, based on 100 parts by mass of the binder.

The coating agent usually contains a dispersion medium. As the dispersion medium, both aqueous and oily media can be used. Examples of the oily medium include hydrocarbon-based solvents such as toluene and xylene; ketone-based solvents such as methyl ethyl ketone and methyl isobutyl ketone; ester-based solvents such as ethyl acetate and butyl acetate; ether-based solvents such as dioxane and ethylene glycol diethyl ether; and the like. Examples of the aqueous medium include water and alcohol-based solvents.

Furthermore, the coating agent may contain other additives such as curing agents, coloring agents, antistatic agents, and leveling agents.

A base material to be coated with the coating agent is not particularly limited, but base materials depending on use can be used. For example, in optical use, transparent materials such as glass base materials and transparent resin base materials are used.

(b) Master Pellet

A master pellet contains the hollow particles and a base material resin.

The base material resin is not particularly limited, as long as it is an ordinary thermoplastic resin. Examples thereof include (meth)acrylic resins, alkyl (meth)acrylate-styrene copolymer resins, polycarbonate resins, polyester resins, polyethylene resins, polypropylene resins, polystyrene resins, and the like. In particular, when transparency is required, (meth)acrylic resins, alkyl (meth)acrylate-styrene copolymer resins, polycarbonate resins, and polyester resins are suitable. These base material resins each can be used alone, or can be used by combining two or more of them. In addition, the base material resin may contain a very small amount of additives such as ultraviolet absorbing agents, heat stabilizers, coloring agents, and fillers.

The master pellet can be produced by a molding method such as extrusion molding and injection molding, by melting and kneading the hollow particles and base material resin. The blending ratio of the hollow particles in the master pellet is not particularly limited, but is preferably about 0.1 to 60% by mass, more preferably about 0.3 to 30% by mass, and further preferably about 0.4 to 10% by mass. If the blending ratio is above 60% by mass, production of the master pellet may become difficult. On the other hand, if the blending ratio is below 0.1% by mass, the effect of the present invention may be deteriorated.

The master pellet becomes a molded article, for example, by extrusion molding, injection molding or press molding. Furthermore, upon molding, the base material resin may be further added. The base material resin is suitably added so that the blending ratio of the hollow particles contained in the finally resulting molded article becomes about 0.1 to 60% by mass. In addition, at the time of molding, for example, additives such as ultraviolet absorbing agents, heat stabilizers, coloring agents, and fillers may be added at a very small amount.

(c) Cosmetic Material

Examples of a specific cosmetic material into which the hollow particles can be blended include solid cosmetic materials such as face powder and foundation; powdery cosmetic materials such as baby powder and body powder; liquid cosmetic materials such as skin lotion, milky lotion, cream, and body lotion; and the like.

The ratio of blending the hollow particles into these cosmetic materials is different depending on a kind of the cosmetic material. For example, for solid cosmetic materials such as face power and foundation, the blending ratio is preferably 1 to 20% by mass, and particularly preferably 3 to 15% by mass. Additionally, for powdery cosmetic materials such as baby powder and body powder, the blending ratio is preferably 1 to 20% by mass, and particularly preferably 3 to 15% by mass. Furthermore, for liquid cosmetic materials such as skin lotion, milky lotion, cream, liquid foundation, body lotion, and pre-shave lotion, the blending ratio is preferably 1 to 15% by mass, and particularly preferably 3 to 10% by mass.

Furthermore, to these cosmetics can be added inorganic compounds such as mica and talc; coloring pigments such as iron oxide, titanium oxide, ultramarine, Prussian blue, and carbon black; synthetic dyes such as an azo-based synthetic dye; or the like, in order to improve the optical function or to improve the sense of touch. For the liquid cosmetic materials, a liquid medium is not particularly limited, but water, alcohols, hydrocarbons, silicone oils, vegetable or animal fats or oils, and the like can also be used. Various functions can also be added to these cosmetic materials by adding moisturizing agents, anti-inflammatory agents, whitening agents, UV care agents, germicides, antiperspirants, refrigerants, perfumes, and the like, which are generally used in cosmetics, in addition to the above-mentioned other ingredients.

(d) Heat-Insulating Film

A heat-insulating film contains at least the above-mentioned hollow particles. Since films or sheet-shaped articles containing the above-mentioned hollow particles have an air layer inside the hollow particles, they can be used as a heat-insulating film. Furthermore, since a particle diameter of the above-mentioned hollows particles is small, a heat-insulating film having high transparency is obtained, and since the binder hardly enters the hollow part, a heat-insulating film having high heat insulating property is easily obtained. The above-mentioned heat-insulating film can be obtained by coating the above-mentioned coating agent on a base material by the well-known method such as a dip method, a spraying method, a spin coating method, a spinner method, and a roll coating method, drying the base material, and if necessary, performing heating, ultraviolet irradiation or firing.

(e) Antireflection Film

An antireflection film contains at least the above-mentioned hollow particles. Since a refractive index of films or sheet-shaped articles containing the above-mentioned hollow particles is reduced due to an air layer inside the hollow particles, they can be used as an antireflection film. Furthermore, since the above-mentioned hollow particles have high heat resistance, an antireflection film having high heat resistance is obtained. The above-mentioned antireflection film can be obtained by coating the above-mentioned coating agent on a base material by the well-known method such as a dip method, a spraying method, a spin coating method, a spinner method, and a roll coating method, drying the base material, and if necessary, performing heating, ultraviolet irradiation or firing.

(f) Base Material with Antireflection Film

A base material with an antireflection film is configured by forming the above-mentioned antireflection film on the surface of a base material such as glass, and plastic sheets, plastic films, plastic lenses, and plastic panels of polycarbonate, acrylic resin, PET, TAC or the like, or a base material of cathode-ray tubes, fluorescent display tubes, liquid crystal display plates or the like. Although different depending on intended use, a film alone is formed on the base material, or is formed on the base material in combination with a protective film, a hard coat film, a flattening film, a high refractive index film, an insulating film, an electrically conductive resin film, an electrically conductive metal fine particle film, an electrically conductive metal oxide fine particle film, or a primer film which is used as necessary, or the like. In addition, when used in combination, it is not necessary that an antireflection film be necessarily formed on an outermost surface.

(g) Light Extraction Film

A light extraction film contains at least the above-mentioned hollow particles. Since in LED or organic EL illumination, a difference in a refractive index between an air layer and a light emitting layer is great, emitted light is easily confined inside an element. For that reason, a light extraction film is used for the purpose of improving the light emitting efficiency. Since in films or sheet-shaped articles containing the above-mentioned hollow particles, a refractive index is reduced due to an air layer inside the hollow particles, they can be used as a light extraction film. Furthermore, since the above-mentioned hollow particles have high heat resistance, a light extraction film having high heat resistance is obtained. The above-mentioned light extraction film can be obtained by coating the above-mentioned coating agent on a base material by the well-known method such as a dip method, a spraying method, a spin coating method, a spinner method, and a roll coating method, drying the base material, and further performing heating, ultraviolet irradiation or firing, as necessary.

(h) Base Material with Light Extraction Film

A base material with a light extraction film is configured by forming the above-mentioned light extraction film on the surface of a base material such as glass, and plastic sheets, plastic films, plastic lenses, and plastic panels of polycarbonate, acrylic resin, PET, TAC or the like, or a base material of cathode-ray tubes, fluorescent display tubes, liquid crystal display plates or the like. Although different depending on intended use, a film alone is formed on the base material, or is formed on the base material in combination with a protective film, a hard coat film, a flattening film, a high refractive index film, an insulating film, an electrically conductive resin film, an electrically conductive metal fine particle film, an electrically conductive metal oxide fine particle film, or a primer film which is used as necessary, or the like. In addition, when used in combination, it is not necessary that a light extraction film be necessarily formed on an outermost surface.

(9) Method for Producing Hollow Particles

The hollow particles can be produced, for example, by passing through a step of preparing polymer particles containing a non-reactive solvent (polymerization step), a step of phase-separating the non-reactive solvent from the polymer particles (phase separation step), and a step of removing the non-reactive solvent (solvent removal step), without particular limitation.

In the conventional method for producing the hollow particles, a shell is formed by polymerizing a reactive monomer once, and phase separation between an organic solvent (non-reactive solvent) and the shell is performed at the same time with polymerization. The inventors of the present invention thought that in this method, a step of performing phase separation and polymerization at the same time causes generation of pinholes and reduction in monodispersity. Furthermore, the inventors thought that pinholes of the shell block reduction in heat conductivity of films and reduction in the reflectance of films when the hollow particles are used as a heat conductivity adjusting agent. Accordingly, the inventors thought that if polymer particles are formed once before phase separation of the non-reactive solvent, and after that, phase separation is generated, generation of pinholes can be suppressed and monodispersity can be improved.

Specifically, polymer particles are prepared by polymerizing a reactive monomer having a radical reactive functional group and a non-radical reactive functional group, based on either of both functional groups. The polymer particles are made to contain the non-reactive solvent, by mixing it with a reactive monomer in advance, or making it absorbed after preparation of the polymer particles. Then, phase separation between the polymer and the non-reactive solvent by polymerization with the other remaining functional group of both functional groups affords microcapsule particles including the non-reactive solvent. After that, removal of the non-reactive solvent affords hollow particles.

In the above-mentioned method, separation of polymerization and phase separation provides advantages that:

Gaps between polymers in the shell, having existed in the conventional production method, disappear, and generation of pinholes in the shell of the resulting hollow particles can be suppressed;

Since a shape of the hollow particles depends on not oil droplets, but a shape and a particle size distribution of the polymer particles before phase separation, hollow particles having high monodispersity are easily obtained.

Explanation of the production method will be described below.

(A) Polymerization Step

In a polymerization step, polymer particles are prepared by polymerizing the reactive monomer having a radical reactive functional group and a non-radical reactive functional group, based on either of both functional groups. The polymer particles are made to contain the non-reactive solvent, by mixing it with the reactive monomer in advance, or making it absorbed after preparation of the polymer particles.

(a) Method for Preparing Polymer Particles

As a method for preparing polymer particles, arbitrary method can be adopted, among the known methods such as a mass polymerization method, a solution polymerization method, a dispersion polymerization method, a suspension polymerization method, and an emulsion polymerization method. Among them, a suspension polymerization method and an emulsion polymerization method, by which polymer particles can be prepared relatively simply, are preferable. Furthermore, an emulsion polymerization method, by which polymer particles having high monodispersity are easily obtained, is more preferable.

The polymer particles are obtained by polymerizing a radical reactive functional group or a non-radical reactive functional group.

In polymerization, it is preferable to add a compound that polymerizes a functional group to be polymerized.

(i) When the radical reactive functional group is polymerized, a polymerization initiator can be used as this compound. Examples of the polymerization initiator are not particularly limited to, but include persulfuric acid salts such as ammonium persulfate, potassium persulfate, and sodium persulfate; organic peroxides such as cumene hydroperoxide, di-tert-butyl peroxide, dicumyl peroxide, benzoyl peroxide, lauroyl peroxide, dimethylbis(tert-butylperoxy)hexane, dimethylbis(tert-butylperoxy)hexyne-3, bis(tert-butylperoxyisopropyl) benzene, bis(tert-butylperoxy)trimethylcyclohexane, butyl-bis(tert-butylperoxy)valerate, tert-butyl 2-ethylhexaneperoxoate, dibenzoyl peroxide, paramenthane hydroperoxide, and tert-butyl peroxybenzoate; and azo compounds such as 2,2-azobis[2-(2-imidazolin-2-yl) propane]dihydrochloride, 2,2-azobis[2-(2-imidazolin-2-yl)propane]disulfate dihydrate, 2,2-azobis(2-amidinopropane) dihydrochloride, 2,2-azobis[N-(2-carboxyethyl)-2-methylpropionamidine]hydrate, 2,2-azobis{2-[1-(2-hydroxyethyl)-2-imidazolin-2-yl] propane}dihydrochloride, 2,2-azobis[2-(2-imidazolin-2-yl)propane], 2,2-azobis(1-imino-1-pyrrolidino-2-ethylpropane) dihydrochloride, 2,2-azobis{2-methyl-N-[1,1-bis(hydroxymethyl)-2-hydroxyethyl] propionamide}, 2,2-azobis[2-methyl-N-(2-hydroxyethyl)propionamide], 4,4-azobis(4-cyanopentanoic acid), 2,2'-azobisisobutyronitrile, 2,2'-azobis(2-methyl-butyronitrile), 2,2'-azobis(2-isopropylbutyronitrile), 2,2'-azobis(2,3-dimethylbutyronitrile), 2,2'-azobis(2,4-dimethylbutyronitrile), 2,2'-azobis(2-methylcapronitrile), 2,2'-azobis(2,3,3-trimethylbutyronitrile), 2,2'-azobis(2,4,4-trimethylvaleronitrile), 2,2-azobis(2,4-dimethylvaleronitrile), 2,2'-azobis(2,4-dimethyl-4-ethoxyvaleronitrile), 2,2'-azobis(2,4-dimethyl-4-n-butoxyvaleronitrile), 2,2'-azobis(4-methoxy-2,4-dimethylvaleronitrile), 2,2'-azobis[N-(2-propenyl)-2-methylpropionamide], 2,2'-azobis(N-butyl-2-methylpropionamide), 2,2'-azobis(N-cyclohexyl-2-methylpropionamide), 1,1-azobis(1-acetoxy-1-phenylethane), 1,1'-azobis(cyclohexane-1-carbonitrile), dimethyl-2,2'-azobis(2-methylpropinate), dimethyl-2,2'-azobisisobutyrate, dimethyl-2,2'-azobis(2-methylpropinate), 2-(carbamoylazo) isobutyronitrile, and 4,4'-azobis(4-cyanovaleric acid). Only one of the polymerization initiators may be used, or two or more of them may be used concurrently.

Alternatively, a redox-based initiator that is a combination of a polymerization initiator such as the above-mentioned persulfuric acid salts and organic peroxides, with a reducing agent such as sodium sulfoxylate formaldehyde, sodium hydrogen sulfite, ammonium hydrogen sulfite, sodium thiosulfate, ammonium thiosulfate, hydrogen peroxide, sodium hydroxymethanesulfinate, L-ascorbic acid and salts thereof, cuprous salt, and ferrous salt may be used as the polymerization initiator.

When polymerization is emulsion polymerization, it is preferable that the polymerization initiator is a water-soluble polymerization initiator that allows emulsion polymerization under a water solvent. The water-soluble polymerization initiator is not particularly limited, but examples thereof include persulfuric acid salts such as ammonium persulfate, potassium persulfate, and sodium persulfate; and azo compounds such as 2,2-azobis[2-(2-imidazolin-2-yl)propane]dihydrochloride, 2,2-azobis[2-(2-imidazolin-2-yl)propane] disulfate dihydrate, 2,2-azobis(2-amidinopropane) dihydrochloride, 2,2-azobis[N-(2-carboxyethyl)-2-methylpropionamidine]hydrate, 2,2-azobis{2-[1-(2-hydroxyethyl)-2-imidazolin-2-yl]propane}dihydrochloride, 2,2-azobis[2-(2-imidazolin-2-yl)propane], 2,2-azobis(1-imino-1-pyrrolidino-2-ethylpropane) dihydrochloride, 2,2-azobis{2-methyl-N-[1,1-bis(hydroxymethyl)-2-hydroxyethyl] propionamide}, 2,2-azobis[2-methyl-N-(2-hydroxyethyl) propionamide], and 4,4-azobis(4-cyanopentanoic acid).

(ii) It is preferable that by polymerizing a radical reactive functional group first, the polymer particles have an unreacted non-radical reactive functional group in a polymer. When a non-radical reactive functional group is polymerized first, it may become difficult to absorb a non-reactive solvent.

It is preferable that by polymerizing one reactive functional group of the radical reactive functional group and non-radical reactive functional group, the polymer particles have the other unreacted reactive functional group in a polymer. However, even when a total amount of a functional group to be polymerized at the time of production of the polymer particles is not polymerized, and the functional group is partially polymerized, there is no severe problem, and even when a part of the other polymerization functional group is polymerized, there is no severe problem. For example, when a radical reactive functional group of glycidyl methacrylate is polymerized to prepare polymer particles having an epoxy group, an unreacted radical reactive functional group may remain, or a partial ring-opening reaction of an epoxy group may occur (in other words, it is only necessary that an epoxy group at an amount enabling phase separation remain in the polymer particles).

An upper limit of a use amount of a chain transfer agent is 50 parts by mass, based on 100 parts by mass of the reactive monomer.

(iii) The chain transfer agent may be used at the time of polymerization of the reactive monomer. The chain transfer agent is not particularly limited, but examples thereof include alkylmercaptans such as n-hexylmercaptan, n-octylmercaptan, t-octylmercaptan, n-dodecylmercaptan, and t-dodecylmercaptan; phenol-based compounds such as α-methylstyrene dimer, 2,6-di-t-butyl-4-methylphenol, and styrenated phenol; allyl compounds such as allyl alcohol; and halogenated hydrocarbon compounds such as dichloromethane, dibromomethane, and carbon tetrachloride. Only one of the chain transfer agents may be used, or two or more of them may be used concurrently.

(b) Absorption of Non-Reactive Solvent

Absorption of the non-reactive solvent into the polymer particles can be performed at the time of production of the polymer particles or after production thereof. Furthermore, absorption of the non-reactive solvent can be performed in the presence or absence of a dispersion medium that is not compatible with the non-reactive solvent. It is preferable that absorption is performed in the presence of the dispersion medium because absorption of the non-reactive solvent can be effectively performed. When a method for producing the polymer particles uses a medium, the medium may be used as the dispersion medium as it is, or after the polymer particles are isolated from the medium once, the particles may be dispersed in the dispersion medium.

To the dispersion medium containing the polymer particles is added a non-reactive solvent that is not compatible with the dispersion medium, and the non-reactive solvent can be absorbed into the polymer particles by performing stirring or the like for a certain time.

Furthermore, absorption of the non-reactive solvent at the time of production of the polymer particles can be achieved by selecting a suitable dispersion medium and non-reactive solvent at the time of preparation of the polymer particles. For example, when polymer particles are prepared by emulsion polymerization under a water solvent, a non-reactive solvent that is not compatible with water is added to the water solvent in advance, and a reactive monomer is polymerized, thereby, preparation of the polymer particles and absorption into the polymer particles can be performed at the same time. When preparation of the polymer particles and absorption into the polymer particles are performed at the same time, the time it takes for absorption of the non-reactive solvent can be reduced.

(i) Dispersion Medium

A dispersion medium is not particularly limited, as long as it is a liquid that does not completely dissolve the polymer particles. Examples thereof include water; alcohols such as ethyl alcohol, methyl alcohol, and isopropyl alcohol; alkanes such as butane, pentane, hexane, cyclohexane, heptane, decane, and hexadecane; aromatic hydrocarbons such as toluene and xylene; ester-based solvents such as ethyl acetate and butyl acetate; ketone-based solvents such as methyl ethyl ketone and methyl isobutyl ketone; and halogen-based solvents such as methyl chloride, methylene chloride, chloroform, and carbon tetrachloride. Only one of these may be used, or two or more of them may be used concurrently.

(ii) Non-Reactive Solvent

A non-reactive solvent is not particularly limited, as long as it is a liquid that is not compatible with a dispersion medium. Being not compatible with a dispersion medium herein means that solubility (at 25° C.) of the non-reactive solvent in the dispersion medium is 10% by mass or less. For example, when water is used as the dispersion medium, examples of a usable non-reactive solvent include butane, pentane, hexane, cyclohexane, heptane, decane, hexadecane, toluene, xylene, ethyl acetate, butyl acetate, methyl ethyl ketone, methyl isobutyl ketone, 1,4-dioxane, methyl chloride, methylene chloride, chloroform, carbon tetrachloride, and the like. Only one of these may be used, or two or more of them may be used concurrently.

An addition amount of the non-reactive solvent is not particularly limited, but is 20 to 5,000 parts by mass, based on 100 parts by mass of the polymer particles. When an addition amount is less than 20 parts by mass, a hollow part of the resulting hollow particles becomes small, and desired properties may not be obtained. When an addition amount exceeds 5,000 parts by mass, a hollow part becomes too big, and the strength of the resulting hollow particles may be reduced.

(B) Phase Separation Step

Next, the remaining reactive functional group is polymerized, and the polymer and the non-reactive solvent are phase-separated. Phase separation affords microcapsule particles including the non-reactive solvent. In addition, in the present invention, it is intended that hollow of the hollow particles includes not only the case where the air exists in a hollow part, but also microcapsule particles in which the non-reactive solvent or another dispersion medium exists in the hollow part.

As a compound that is added to polymerize the remaining reactive functional group, the same compounds as the polymerization initiators for polymerizing the radical reactive functional group and the crosslinking agents for polymerizing the non-radical reactive functional group, described in the above-mentioned polymerization step, can be used.

(C) Solvent Removal (Replacement) Step

Hollow particles in which the air or another solvent exists in the hollow part can be obtained, by removing or replacing the non-reactive solvent included in microcapsule particles, as necessary. A method for removing the non-reactive solvent is not particularly limited, but examples thereof include a reduced pressure drying method and the like. Examples of the conditions for the reduced pressure drying method include the pressure of 500 Pa or less, 30 to 200° C., and 30 minutes to 50 hours. Alternatively, the non-reactive solvent can be replaced by a solvent replacement operation. For example, a suitable dispersion medium is added to microcapsule particles including the non-reactive solvent, or a dispersion thereof, and stirring or the like is performed, thereby, the non-reactive solvent inside the particles is replaced with a dispersion medium. Thereafter, the non-reactive solvent can be replaced by removing the extra non-reactive solvent and dispersion medium by a reduced pressure drying method, a centrifugal separation method, an ultrafiltration method or the like. Solvent replacement may be performed only once, or plural times.

The hollow particles may be used as a dispersion of hollow particles in a solvent, as necessary. For example, the hollow particles may be used in the state of a dispersion of microcapsule particles including the non-reactive solvent, obtained after a phase separation step, or may be used as a dispersion in a solvent replaced with another dispersion solvent.

The hollow particles may be used as a dry powder obtained by drying the dispersion of the hollow particles in a solvent, as necessary. A method of drying the hollow particles is not particularly limited, but examples thereof include a reduced pressure drying method and the like. In addition, a dispersion solvent, a non-reactive solvent or the like which remained without being dried, may remain in the dry powder.

(D) Other Step(s)

By adding a compound having an anionic group to the dispersion of the hollow particles after a phase separation step, and stirring the materials, or adding a compound having an anionic group to the hollow particles after a solvent removal step, and mixing the materials, the surface of the hollow particles can be treated with the compound having an anionic group. Inter alia, it is preferable that after the extra crosslinking agent is removed after a phase separation step, the compound having an anionic group is added to the dispersion of the hollow particles, and the materials are stirred Examples of the treatment conditions include 30 to 200° C., and 30 minutes to 50 hours.

Furthermore, by adding a silicon-based compound, a titanate-based coupling agent, an aluminate-based coupling agent, a zirconate-based coupling agent, an isocyanate-based compound or the like into the dispersion of the hollow particles after the phase separation step, and stirring the materials, or adding a silicon-based compound, a titanate-based coupling agent, an aluminate-based coupling agent, a zirconate-based coupling agent, an isocyanate-based compound or the like to the hollow particles after the solvent removal step, and mixing the materials, the surface of the hollow particles can be treated with a silicon-based compound, a titanate-based coupling agent, an aluminate-based coupling agent, a zirconate-based coupling agent, an isocyanate-based compound or the like. Inter alia, it is preferable that the hollow particles are treated with the compound having an anionic group, and after that, treated with a silicon-based compound, a titanate-based coupling agent, an aluminate-based coupling agent, a zirconate-based coupling agent, an isocyanate-based compound or the like. Examples of the treatment conditions include 30 to 200° C., and 30 minutes to 50 hours.

EXAMPLES

The present invention will be illustrated more specifically below by way of Examples, but the present invention is not limited to these at all. First, details of various measurement methods used in Examples will be described below.

(Average Particle Diameter, Hollow Ratio, CV Value)

An average particle diameter, a hollow ratio, and a CV value of the hollow particles are measured as follows.

That is, 10% by mass of a dispersion of hollow particles in methyl alcohol is dried with a vacuum drier at 60° C. for 4 hours to obtain a dry powder. A TEM photograph of the hollow particles is taken at magnification of about 300,000 under the conditions of an acceleration voltage of 80 kV using a transmission electron microscope (H-7600 manufactured by Hitachi High-Technologies Corporation). At that time, by using ruthenium tetroxide staining or the like, particles can be identified more clearly. A particle diameter and an inner diameter of random 100 or more particles, shown in this photograph, are observed. At this time, by measuring a particle diameter and an inner diameter of 5 or more places so as to pass through the center of the particle, and averaging them, an average particle diameter and an average inner diameter are obtained. Furthermore, by the equation of (average inner diameter)$^3$/(average particle diameter)$^3 \times 100$, a hollow ratio of the hollow particles is obtained.

Furthermore, in regard to a coefficient of variation (CV value) of a particle diameter of the hollow particles, a standard deviation and an average particle diameter of the above-mentioned particle diameter are obtained, and further, a value obtained by the equation of (standard deviation)/(average particle diameter)$\times 100$ is defined as a CV value of the hollow particles.

(Refractive Index)

A refractive index of an N-containing resin constituting a shell of the hollow particles is obtained as follows.

That is, a refractive index nm of methyl alcohol adjusted at 20° C., and a refractive index $n_a$ of 10% by mass of a dispersion of the hollow particles in methyl alcohol are measured with an Abbe refractometer (NAR-IT) manufactured by ATAGO CO., LTD. Letting the specific gravity of methyl alcohol and that of the shell of the hollow particles to be 0.792 and 1.17 respectively, volume % at that time is represented by q, and the equation of Maxwell-Garnett is used to calculate a refractive index $n_p$ Of an N-containing resin constituting the shell of the hollow particles.

$$(n_a^2 - n_m^2)/(n_a^2 + 2n_m^2) = q(n_p^2 - n_m^2)/(n_p^2 + 2n_m^2)$$ [Equation of Maxwell-Garnett]

In addition, for assessment of a refractive index, if a refractive index is 1.57 or less, this is determined to be ○, and if a refractive index is greater than 1.57, this is determined to be x.

(N/C) and (Si/C)

(N/C) and (Si/C) of an N-containing resin, and those of a Si & N-containing resin are measured as follows.

That is, a 10 wt % dispersion of the hollow particles in methyl alcohol is dried with a vacuum drier at 60° C. for 4 hours, to obtain a dry powder, and after that, the powder is compression molded with a tablet molding machine for IR to prepare a test piece. With regard to the test piece, the abundance ratio of a nitrogen atom, N [atom %], and the abundance ratio of a carbon atom C [atom %], and the abundance ratio of a silicon atom, Si [atom %], of the N-containing resin and the Si & N-containing resin are measured under the measurement conditions of measurement range: wide spectrum (1,350 to 0 eV), photoelectron intake angle 90 degrees, and path energy: wide spectrum 160 eV or 80 eV, using an X-ray photoelectron spectrometric analysis apparatus, XPS (KRATOS AXIS-ULTRA DLD manufactured by Shimadzu Corporation). By dividing measured N and Si by C, (N/C) and (Si/C) are calculated.

In addition, for assessment of N/C, 0.03 to 0.2 is determined to be ○, and less than 0.03 or greater than 0.2 is determined to be x. For assessment of Si/C, 0.002 to 0.1 is determined to be ○, and less than 0.002 or greater than 0.1 is determined to be X.

(Reflectance)

The reflectance of a film using the hollow particles is measured as follows.

That is, 20 parts by mass of a 10 mass % dispersion of the hollow particles in methyl alcohol, 4 parts by mass of dipentaerythritol polyacrylate (NK Ester A-9570W manufactured by SHIN-NAKAMURA CHEMICAL CO., LTD.), 0.20 parts by mass of a photopolymerization initiator (IRGACURE1173 manufactured by BASF company), and 0.50 parts by mass of a phosphoric acid ester-based surfactant (Plysurf A-208F manufactured by Daiichi Kogyo Seiyaku Co., Ltd.) are mixed, and the mixture is forcibly stirred for 5 minutes using an ultrasound homogenizer (Model SONIFIER450 manufactured by BRANSON Company) to obtain a mixed solution. The mixed solution (0.5 ml) is added dropwise to a slide glass (S1111 manufactured by Matsunami Glass Ind., Ltd.), and coating is performed using a spin coater (Model K-359SD1 manufactured by KYOWA RIKEN CO., LTD.) to obtain a coated film. The resulting coated film is dried at room temperature (about 25° C.) under an ambient pressure. The dried coated film is passed through an ultraviolet irradiation device (J-Cure manufactured by JATEC Co., Ltd., Model JU-C1500, drawing speed: 0.4 m/min, peak illuminance: 125 mW/cm$^2$) three times to harden, thereby, a film is prepared.

Using an ultraviolet-visible spectrophotometer (manufactured by Shimadzu Corporation, Model UV-2450) equipped with an integrating sphere (manufactured by Shimadzu Corporation, Model ISR-2200), the reflectance from an upper surface of the film from a light source 550 nm, an incident angle 8°, is measured.

In addition, for assessment of the reflectance of the film, if the reflectance is 8.0% or less, this is determined to be ○, and if the reflectance is greater than 8.0%, this is determined to be x. In addition, the reflectance of only the slide glass is 8.4%, and the reflectance of a film prepared only with dipentaerythritol polyacrylate with no hollow particles added thereto is 8.3%.

Example 1

Into a 1 L reactor equipped with a stirrer and a thermometer, 35 parts by mass of glycidyl methacrylate, 5 parts by mass of 3-methacryloxypropyltriethoxysilane, 0.8 parts by mass of n-octylmercaptan, and 40 parts by mass of toluene were placed, and the materials were mixed. Next, an aqueous phase obtained by dissolving 0.8 parts by mass of sodium p-styrenesulfonate and 0.4 parts by mass of potassium persulfate in 720 parts by mass of ion-exchanged water was added. Heating the mixed solution at 70° C. for 10 hours while stirring gave polymer particles containing a remaining epoxy group. Since toluene had been added to emulsion polymerization, the polymer particles containing a remaining epoxy group were swollen with toluene.

Next, to polymerize the remaining epoxy group, 20 parts by mass of ethylenediamine was added, and polymerization was performed at 70° C. for 24 hours. By a reaction of an epoxy group in the polymer particles, the polymer and toluene phase-separated, and a dispersion of microcapsule particles was obtained. The resulting dispersion was washed with ion-exchanged water three times, excessive ethylene diamine was removed, thereafter, ion-exchanged water was added so that the solid content became 10% by mass, and a 10 mass % dispersion of hollow particles in water was obtained. To 400 parts by mass of the resulting 10 mass % dispersion of hollow particles in water was added 4.7 parts by mass of 20 wt % aqueous hydrochloric acid, and the mixture was stirred at room temperature for 1 hour, thereby, surface-treated hollow particles were obtained. Next, the particles were washed with methyl alcohol three times, removal of toluene in the interior and washing of unnecessary materials were performed, thereafter, methyl alcohol was appropriately added so that the solid content became 10% by mass, and a 10 mass % dispersion of hollow particles in methyl alcohol was obtained.

The resulting hollow particles had an average particle diameter of 65 nm and a CV value of 17%, and were hollow particles having high monodispersity. Furthermore, a hollow ratio was as high as 34%, and a refractive index of the shell was as low as 1.54. N/C was 0.06 and Si/C was 0.007.

Furthermore, when the resulting hollow particles were used to prepare a film, and the reflectance was measured, the film had the reflectance of 7.2%, and was excellent in the low reflectivity.

Example 2

By changing an addition amount of glycidyl methacrylate to 30 parts by mass, and an addition amount of potassium persulfate to 1.2 parts by mass, adding 5 parts by mass of methyl methacrylate, and performing treatment with 5.1 parts by mass of dodecanoic acid (lauric acid) in place of 4.7 parts by mass of 20 wt % aqueous hydrochloric acid, surface-treated hollow particles were obtained.

The resulting hollow particles had an average particle diameter of 64 nm and a CV value of 17%, and were hollow particles having high monodispersity. Furthermore, a hollow ratio was as high as 30%, and a refractive index of the shell was as low as 1.53. N/C was 0.05 and Si/C was 0.006.

Furthermore, when the resulting hollow particles were used to prepare a film, and the reflectance was measured, the film had the reflectance of 7.3%, and was excellent in the low reflectivity.

Example 3

According to the same manner as that of Example 1 except that treatment was performed with 5.9 parts by mass of 2-methacryloyloxyethylsuccinic acid in place of 4.7 parts by mass of 20 wt % aqueous hydrochloric acid, surface-treated hollow particles were obtained.

The resulting hollow particles had an average particle diameter of 65 nm and a CV value of 17%, and were hollow particles having high monodispersity. Furthermore, a hollow ratio was as high as 34%, and a refractive index of the shell was as low as 1.53. N/C was 0.05 and Si/C was 0.005.

Furthermore, when the resulting hollow particles were used to prepare a film, and the reflectance was measured, the film had the reflectance of 7.2%, and was excellent in the low reflectivity.

Example 4

According to the same manner as that of Example 1 except that treatment was performed with 9.3 parts by mass of dodecylbenzenesulfonic acid in place of 4.7 parts by mass of 20 wt % aqueous hydrochloric acid, surface-treated hollow particles were obtained.

The resulting hollow particles had an average particle diameter of 65 nm and a CV value of 17%, and were hollow particles having high monodispersity. Furthermore, a hollow ratio was as high as 34%, and a refractive index of the shell was as low as 1.54. N/C was 0.04 and Si/C was 0.004.

Furthermore, when the resulting hollow particles were used to prepare a film, and the reflectance was measured, the film had the reflectance of 7.1%, and was excellent in the low reflectivity.

Example 5

According to the same manner as that of Example 1 except that treatment was performed with 12.5 parts by mass of Phosmer PP (manufactured by Uni Chemical Co., Ltd., acid phosphooxypolyoxypropylene glycol monomethacrylate) in place of 4.7 parts by mass of 20 wt % aqueous hydrochloric acid, surface-treated hollow particles were obtained.

The resulting hollow particles had an average particle diameter of 66 nm and a CV value of 16%, and were hollow particles having high monodispersity. Furthermore, a hollow ratio was as high as 35%, and a refractive index of the shell was as low as 1.53. N/C was 0.04 and Si/C was 0.004.

Furthermore, when the resulting hollow particles were used to prepare a film, and the reflectance was measured, the film had the reflectance of 7.1%, and was excellent in the low reflectivity.

Example 6

According to the same manner as that of Example 1 except that treatment was performed with 22.9 parts by mass of polyoxyethylene alkyl ether phosphoric acid (RS-710 manufactured by TOHO Chemical Industry Co., Ltd.) in place of 4.7 parts by mass of 20 wt % aqueous hydrochloric acid, surface-treated hollow particles were obtained.

The resulting hollow particles had an average particle diameter of 66 nm and a CV value of 16%, and were hollow particles having high monodispersity. Furthermore, a hollow ratio was as high as 35%, and a refractive index of the shell was as low as 1.53. N/C was 0.04 and Si/C was 0.004.

Furthermore, the resulting hollow particles were used to prepare a film, and the reflectance was measured, the film had the reflectance of 7.1%, and was excellent in the low reflectivity.

Comparative Example 1

According to the same manner as that of Example 1 except that 40 parts by mass of dipentaerythritol hexaacrylate was used in place of glycidyl methacrylate and 3-methacryloxypropyltriethoxysilane, ethylenediamine was not used, 0.8 parts by mass of dilauroyl peroxide was used in place of potassium persulfate, 30 parts by mass of toluene and 10 parts by mass of cyclohexane were used in place of toluene, 0.4 parts by mass of sodium dodecylbenzenesulfonate was used in place of sodium p-toluenesulfonate, and surface treatment was not performed, hollow particles were obtained.

The resulting hollow particles had an average particle diameter of 94 nm and a CV value of 42%, and were hollow particles having low monodispersity. Furthermore, a hollow ratio was as high as 35%, and a refractive index of the shell was as low as 1.53. N/C was 0 and Si/C was 0. When the resulting hollow particles were used to prepare a film, and the reflectance was measured, the film had the reflectance of 8.2%, and was inferior in the low reflectivity.

Comparative Example 2

According to the same manner as that of Example 1 except that 40 parts by mass of jER828 (manufactured by Mitsubishi Chemical Corporation, bisphenol A-type liquid epoxy resin, epoxy equivalent 184 to 194) was used in place of glycidyl methacrylate and 3-methacryloxypropyltriethoxysilane, N-2-(aminoethyl)-3-aminopropyltrimethoxysilane was used in place of ethylenediamine, potassium persulfate was not used, 30 parts by mass of toluene and 10 parts by mass of cyclohexane were used in place of toluene, 0.4 parts by mass of sodium dodecylbenzenesulfonate was used in place of sodium p-toluenesulfonate, and surface treatment was not performed, hollow particles were obtained.

The resulting hollow particles had an average particle diameter of 103 nm and a CV value of 39%, and were hollow particles having low monodispersity. Furthermore, a hollow ratio was as high as 32%, and a refractive index of the shell was as high as 1.59. N/C was 0.02 and Si/C was 0.005. When the resulting hollow particles were used to prepare a film, and the reflectance was measured, the film had the reflectance of 8.1%, and was inferior in the low reflectivity.

The following Table 1 and Table 2 show raw materials used in producing the hollow particles, and physical properties altogether.

TABLE 1

| | | | | Example | | | | | | Comparative Example | |
|---|---|---|---|---|---|---|---|---|---|---|---|
| | | | Unit | 1 | 2 | 3 | 4 | 5 | 6 | 1 | 2 |
| Raw material | Reactive monomer | Glycidyl methacrylate | Parts by mass | 35 | 30 | 35 | 35 | 35 | 35 | — | — |
| | | Dipentaerythritol hexaacrylate | Parts by mass | — | — | — | — | — | — | 40 | — |
| | | jER828 | Parts by mass | — | — | — | — | — | — | — | 40 |
| | | 3-Methacryloxy-propyltriethoxysilane | Parts by mass | 5 | 5 | 5 | 5 | 5 | 5 | — | — |
| | | Methyl methacrylate | Parts by mass | — | 5 | — | — | — | — | — | — |
| | Crosslinking agent | Ethylenediamine | Parts by mass | 20 | 20 | 20 | 20 | 20 | 20 | — | — |
| | | N-2 (aminoethyl)-3-aminopropyltrimethoxysilane | Parts by mass | — | — | — | — | — | — | — | 20 |
| | Chain transfer agent | n-octylmercaptan | Parts by mass | 0.8 | 0.8 | 0.8 | 0.8 | 0.8 | 0.8 | — | — |
| | Polymerization initiator | Potassium persulfate | Parts by mass | 0.4 | 1.2 | 0.4 | 0.4 | 0.4 | 0.4 | — | — |
| | | Dilauroyl peroxide | Parts by mass | — | — | — | — | — | — | 0.8 | — |
| | Non-reactive solvent | Toluene | Parts by mass | 40 | 40 | 40 | 40 | 40 | 40 | 30 | 30 |
| | | Cyclohexane | Parts by mass | — | — | — | — | — | — | 10 | 10 |
| | Dispersion auxiliary agent | Sodium p-styrenesulfonate | Parts by mass | 0.8 | 0.8 | 0.8 | 0.8 | 0.8 | 0.8 | — | — |
| | | Sodium dodecylbenzenesulfonate | Parts by mass | — | — | — | — | — | — | 0.4 | 0.4 |
| | Surface treating agent | 20 wt % aqueous hydrochloric acid | Parts by mass | 4.7 | — | — | — | — | — | — | — |
| | | Dodecanoic acid (lauric acid) | Parts by mass | — | 5.1 | — | — | — | — | — | — |
| | | 2-Methacryloyloxyethylsuccinic acid | Parts by mass | — | — | 5.9 | — | — | — | — | — |
| | | Dodecylbenzenesulfonic acid | Parts by mass | — | — | — | 9.3 | — | — | — | — |
| | | Phosmer PP | Parts by mass | — | — | — | — | 12.5 | — | — | — |

TABLE 1-continued

|  | Unit | Example 1 | Example 2 | Example 3 | Example 4 | Example 5 | Example 6 | Comparative Example 1 | Comparative Example 2 |
|---|---|---|---|---|---|---|---|---|---|
| Polyoxyethylene alkyl ether phosphoric acid | Parts by mass | — | — | — | — | — | 22.9 | — | — |

TABLE 2

|  |  | Unit | Example 1 | Example 2 | Example 3 | Example 4 | Example 5 | Example 6 | Comparative Example 1 | Comparative Example 2 |
|---|---|---|---|---|---|---|---|---|---|---|
| Assessment | Average particle diameter | nm | 65 | 64 | 65 | 65 | 66 | 66 | 94 | 103 |
|  | CV value | % | 17 | 17 | 17 | 17 | 16 | 16 | 42 | 39 |
|  | Hollow ratio | % | 34 | 30 | 34 | 34 | 35 | 35 | 35 | 32 |
|  | Shell refractive index/determination | — | 1.54/o | 1.53/o | 1.53/o | 1.54/o | 1.53/o | 1.53/o | 1.53/o | 1.59/x |
|  | N/C/determination | — | 0.06/o | 0.05/o | 0.05/o | 0.04/o | 0.04/o | 0.04/o | 0/x | 0.02/x |
|  | Si/C/determination | — | 0.007/o | 0.006/o | 0.005/o | 0.004/o | 0.004/o | 0.004/o | 0/x | 0.005/x |
|  | Reflectance/determination | % | 7.2/o | 7.3/o | 7.2/o | 7.1/o | 7.1/o | 7.1/o | 8.2/x | 8.1/x |

A photograph of the hollow particles of Example 1 is shown in FIG. 1.

By comparison between Examples 1 to 6 and Comparative Examples 1 to 2 of Table 2, it was seen that the hollow particles which have a small particle diameter, have high monodispersity, and are suitable for preparing a film having the low reflectance can be produced.

Example 7

Antireflection Film•Base Material with Antireflection Film 20 parts by mass of the 10 wt % dispersion of the surface-treated hollow particles in methyl alcohol prepared in Example 1, 4 parts by mass of dipentaerythritol polyacrylate (NK Ester A-9570W manufactured by SHIN-NAKA-MURA CHEMICAL CO., LTD.), 0.20 parts by mass of a photopolymerization initiator (IRGACURE1173 manufactured by BASF Company), and 0.5 parts by mass of a polyether phosphoric acid ester-based surfactant (Solsperse 41000 manufactured by Lubrizol Japan Limited) were mixed, and the mixture was forcibly stirred for 5 minutes using an ultrasound homogenizer (manufactured by BRANSON Company, Model SONIFIER450), to obtain a coating agent. The coating agent (0.5 ml) was added dropwise to a slide glass (S1111 manufactured by Matsunami Glass Ind., Ltd.), and coating was performed using a spin coater (manufactured by KYOWA RIKEN CO., LTD., Model K-359SD1) to obtain a coated film. The resulting coated film was dried at room temperature (about 25° C.) under an ambient pressure. The dried coated film was passed through an ultraviolet irradiation device (J-Cure manufactured by JATEC Co, Ltd., Model JUC1500, drawing speed: 0.4 m/min, peak illuminance 125 mW/cm$^2$) three times to harden, thereby, a base material with an antireflection film, in which an antireflection film is formed on a glass substrate, was prepared. The reflectance of the base material with an antireflection film was 7.2%, and was lower than the reflectance (8.4%) of a slide glass with no antireflection film, and antireflection property was excellent. A method for measuring the reflectance here was the same as the above-mentioned measuring method for the hollow particles.

Example 8

Light Extraction Film•Base Material with Light Extraction Film 20 parts by mass of the 10 wt % dispersion of the surface-treated hollow particles in methyl alcohol prepared in Example 1, 4 parts by mass of dipentaerythritol polyacrylate (NK Ester A-9570W manufactured by SHIN-NAKA-MURA CHEMICAL CO., LTD.), 0.20 parts by mass of a photopolymerization initiator (IRGACURE1173 manufactured by BASF Company), and 0.50 parts by mass of a polyether phosphoric acid ester-based surfactant (Solsperse 41000 manufactured by Lubrizol Japan Limited) were mixed, and the mixture was forcibly stirred for 5 minutes using an ultrasound homogenizer (manufactured by BRANSON Company, Model SONIFIER450) to obtain a coating agent, 0.5 ml of the coating agent was added dropwise to a slide glass (S1111 manufactured by Matsunami Glass Ind., Ltd.), and coating was performed using a spin coater (manufactured by KYOWA RIKEN CO., LTD., Model K-359SD1) to obtain a coated film. The resulting coated film was dried at room temperature (about 25° C.) under an ambient pressure. The dried coated film was passed through an ultraviolet irradiation device (J-Cure manufactured by JATEC Co., Ltd., Model JUC1500, drawing speed: 0.4 m/min, peak illuminance 125 mW/cm$^2$) three times to harden, thereby, a base material with a light extraction film, in which a light extraction film is formed on a glass substrate, was prepared.

When the total light transmittance of the base material with a light extraction film was measured using a haze meter, the total light transmittance of the base material with a light extraction film was 93.4%, and was greater than the total light transmittance (92.0%) of a slide glass with no light extraction film. This is probably because, since the light extraction film contains the hollow particles, a refractive index of the light extraction film was reduced, and since reflection at an air interface was suppressed, the total light transmittance was improved.

The total light transmittance was measured by the following procedure in accordance with the method described in JIS K7361-1: 1997 "Plastics-Determination of the Total Luminous Transmittance of Transparent Materials. —Part 1: Single Beam Instrument."

That is, a haze meter (manufactured by MURAKAMI COLOR RESEARCH LABORATORY CO., Ltd., Model: HM-150) is used to measure the prepared substrate with a light extraction film, by employing a light source (D65), a double beam method, after the light source of the device is stabilized. After a stabilization time of 30 minutes, measurement is performed to check that the light source is stabilized. The test number is 2, and an average thereof is defined as total light transmittance.

Example 9

Light-Guiding Plate Ink•Light-Guiding Plate

The 10 wt % dispersion of the surface-treated hollow particles in methyl alcohol prepared in Example 1, was washed with methyl ethyl ketone three times, to obtain a 10 wt % dispersion of the hollow particles in methyl ethyl ketone, 45 parts by mass of the resulting 10 wt % dispersion of the hollow particles in methyl ethyl ketone, 10 parts by mass of an acrylic-based resin (ACRYDIC A-181 manufactured by DIC CORPORATION, solid content 45%), and 1.0 part by mass of a polyether phosphoric acid ester-based surfactant (Solsperse 41000 manufactured by Lubrizol Japan Limited) were mixed to obtain a light diffusing composition (light-guiding plate ink).

The above-mentioned light diffusing composition was screen-printed on a 5 inch transparent acrylic plate so that a dot pitch became 500 μm, and a diameter of a dot became 50 μm, to obtain a light-guiding plate.

What is claimed is:

1. Hollow particles each having a shell composed of at least one layer, wherein the at least one layer contains a nitrogen atom-containing resin having a refractive index of 1.57 or less;
    wherein the nitrogen atom-containing resin is an organic-inorganic hybrid resin containing a silicon component;
    wherein the nitrogen atom-containing resin is a vinyl-based resin;
    wherein, after the shell is prepared, the shell is surface treated with a compound having at least one anionic group such that the compound having at least one anionic group reacts with the nitrogen atom-containing resin of the shell.

2. The hollow particles according to claim 1, wherein the nitrogen atom-containing resin has an abundance ratio N of a nitrogen atom and an abundance ratio C of a carbon atom satisfying a relationship of 0.03≤N/C≤0.2 in measurement by XPS.

3. The hollow particles according to claim 1, which have an average particle diameter of 10 to 150 nm.

4. The hollow particles according to claim 1, wherein the nitrogen atom-containing resin is a nitrogen atom-containing vinyl-based resin composed of a vinyl-based monomer.

5. The hollow particles according to claim 1, wherein the compound having an anionic group is selected from a carboxylic acid compound, a sulfonic acid compound, and a phosphoric acid ester compound.

6. A dispersion comprising the hollow particles as defined according to claim 1.

7. A coating agent comprising the hollow particles according to claim 1.

8. A heat-insulating film comprising the hollow particles according to claim 1.

9. The heat-insulating film according to claim 8, wherein the heat-insulating film has a reflectance of at most 7.1%.

10. Hollow particles each having a shell composed of at least one layer, wherein the at least one layer contains a nitrogen atom-containing resin having a refractive index of 1.57 or less;
    wherein, after the shell is prepared, the shell is surface treated with a compound having at least one anionic group such that the compound having at least one anionic group reacts with the nitrogen atom-containing resin of the shell; and
    wherein the compound having an anionic group is at least one selected from the group consisting of a sulfonic acid compound and a phosphoric acid ester compound.

11. The hollow particles according to claim 10, wherein the nitrogen atom-containing resin has an abundance ratio N of a nitrogen atom and an abundance ratio C of a carbon atom satisfying a relationship of 0.03≤N/C≤0.2 in measurement by XPS.

12. The hollow particles according to claim 10, wherein the nitrogen atom-containing resin is an organic-inorganic hybrid resin containing a silicon component.

13. The hollow particles according to claim 10, which have an average particle diameter of 10 to 150 nm.

14. The hollow particles according to claim 10, wherein the nitrogen atom-containing resin is a nitrogen atom-containing vinyl-based resin composed of a vinyl-based monomer.

15. A dispersion comprising the hollow particles according to claim 10.

16. A coating agent comprising the hollow particles according to claim 10.

17. A heat-insulating film comprising the hollow particles according to claim 10.

18. The heat-insulating film according to claim 17, wherein the heat-insulating film has a reflectance of at most 7.1%.

19. The hollow particles according to claim 10, wherein the nitrogen atom-containing resin is a polymer derived from a polyamine-based compound.

* * * * *